US00PP27581P2

(12) United States Plant Patent
Chaparro et al.

(10) Patent No.: US PP27,581 P2
(45) Date of Patent: Jan. 24, 2017

(54) MANDARIN TREE NAMED 'UFGLOW'

(50) Latin Name: *Citrus reticulata*
Varietal Denomination: UFGlow

(71) Applicant: Florida Foundation Seed Producers, Inc., Marianna, FL (US)

(72) Inventors: Jose X. Chaparro, Gainesville, FL (US); Wayne B. Sherman, New Smyrna Beach, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/757,086

(22) Filed: Nov. 16, 2015

(51) Int. Cl.
*A01H 5/08* (2006.01)

(52) U.S. Cl.
USPC ..... Plt./202

(58) Field of Classification Search
USPC ..... Plt./156, 201, 202
See application file for complete search history.

(56) References Cited

U.S. PATENT DOCUMENTS

PP21,356 P3 10/2010 Gmitter, Jr. et al.
PP23,724 P2 7/2013 McCollum et al.
PP26,086 P3 11/2015 Grosser

OTHER PUBLICATIONS

U.S. Appl. No. 14/756,644, filed Sep. 28, 2015, Grosser.
U.S. Appl. No. 14/544,780, filed Feb. 12, 2015, Gmitter.

*Primary Examiner* — Susan McCormick Ewoldt
*Assistant Examiner* — Karen Redden
(74) *Attorney, Agent, or Firm* — Dentons US LLP

(57) ABSTRACT

A new and distinct variety of hybrid *citrus* tree, denominated 'UFGlow', bears fruit that ripen in mid October in north central Florida. The tree is evergreen, of medium size, and has a moderately vigorous and semi-spreading growth habit. Trees are self-fertile and bear heavy annual crops of early season fruit that ripen in the second half of October in Gainesville, Fla. Fruit are firm, juicy, sweet tasting, easy peeling, and seedless. Fruit are oblate with a slightly depressed stem end.

2 Drawing Sheets

Latin name of the genus and species of the plant claimed: *Citrus reticulata.*

Variety denomination: 'UFGlow'.

BACKGROUND OF THE INVENTION

The present invention relates to a new and distinct mandarin hybrid [*Citrus reticulata*] tree selected for fresh fruit consumption. This new tree, named 'UFGlow', produces seedless fruit with orange flesh having good fresh fruit eating quality for commercial production in mid October to mid November at Gainesville, Fla. 'UFGlow' is a promising candidate for commercial production in that it produces seedless, easy-peeling fruit that ripen before frost and can be grown in north central Florida and similar climates.

'UFGlow' originated in a cultivated area in Gainesville, Fla. where it was propagated and tested. The female parent of 'UFGlow', [('Clementine'×'Orlando')×'op'] originated as an open pollinated seedling of an F1 hybrid between 'Clementine' (unpatented) mandarin and 'Orlando' (unpatented) Tangelo. The male parent of 'UFGlow' was 'Kishu' (unpatented) mandarin. 'UFGlow' was selected in 2010 in a cold hardy *citrus* breeding program and tested as Fla. 10-02sm. 'UFGlow' was budded onto *P. trifoliata* (L.) Raf. and 'Carrizo' (unpatented) rootstocks. Trees remained true to the original tree and all characteristics of the tree and the fruit have transmitted through an asexual generation.

'UFGlow' was first asexually propagated in Gainesville, Fla. by budding and veneer grafting vegetative material (buds) from the fruiting seedling tree onto juvenile seedlings of standard commercial rootstocks.

'UFGlow' differs from the female parent [('Clementine'× Orlando)×'op'] in that 'UFGlow' ripens earlier, is easier peeling and has no seed. 'UFGlow' is larger fruited and ripens earlier than 'Kishu'. The standard cultivar that ripens at a similar harvest window is 'Fallglo' (unpatented) mandarin and its mutant 'U.S. Early Pride' (U.S. Plant Pat. No. 23,724). Fruit of 'Fallglo' and 'U.S. Early Pride' are larger, more acidic, with a light orange peel color, they are seedy ('Fallglo') or have low seed count ('U.S. Early Pride'), and are more difficult to peel. 'UFGlow' fruit are smaller, contain no seeds, are easier to peel, and have lower acidity. 'Fallglo' and 'U.S. Early Pride' trees suffer from limb dieback similar to 'Robinson' dieback, while 'UFGlow' does not suffer from this problem. The leaves of 'Fallglo' and 'U.S. Early Pride' are narrower, giving the tree a willow leaf aspect. Leaves of 'UFGlow' are broader.

SUMMARY OF THE INVENTION

This new and distinct variety of *citrus* fruit tree bears fruit that ripen in mid October through November in Gainesville, Fla., but should be approximately 4 weeks earlier in the Indian River area of south central Florida. Trees in Gainesville, Fla. have survived freezes of 18° F. without any damage to small branches or leaves. 'UFGlow' is expected to produce a mandarin type fruit in North Central Florida and similar climates. The fruit are uniformly medium-small, averaging 120 grams, juicy, and sweet, with orange flesh.

Trees are vigorous, productive, producing approximately 1 bushel of fruit per tree on 5-year-old trees, self-fruitful, and without alternate bearing. Preliminary experiments indicate the ripe fruit can be stored for at least 24 days using standard mandarin storage conditions.

BRIEF DESCRIPTION OF THE DRAWINGS

The accompanying figures show 'UFGlow' as nearly true as is reasonably possible in a color illustration of this type. The tree, flowers, and fruit may vary in slight detail due to variations in soil type, cultural practices, and climatic condition. The potential for commercial production of fresh fruit by 'UFGlow' is high, due to its mid November ripening, sweet, juicy flesh, easy peeling, and seedless fruit. Colors (except those in common terms) are described according to "The Pantone Book of Color," published by H. N. Abrams, Inc., N.Y. 1990.

DETAILED BOTANICAL DESCRIPTION

Figure 1:
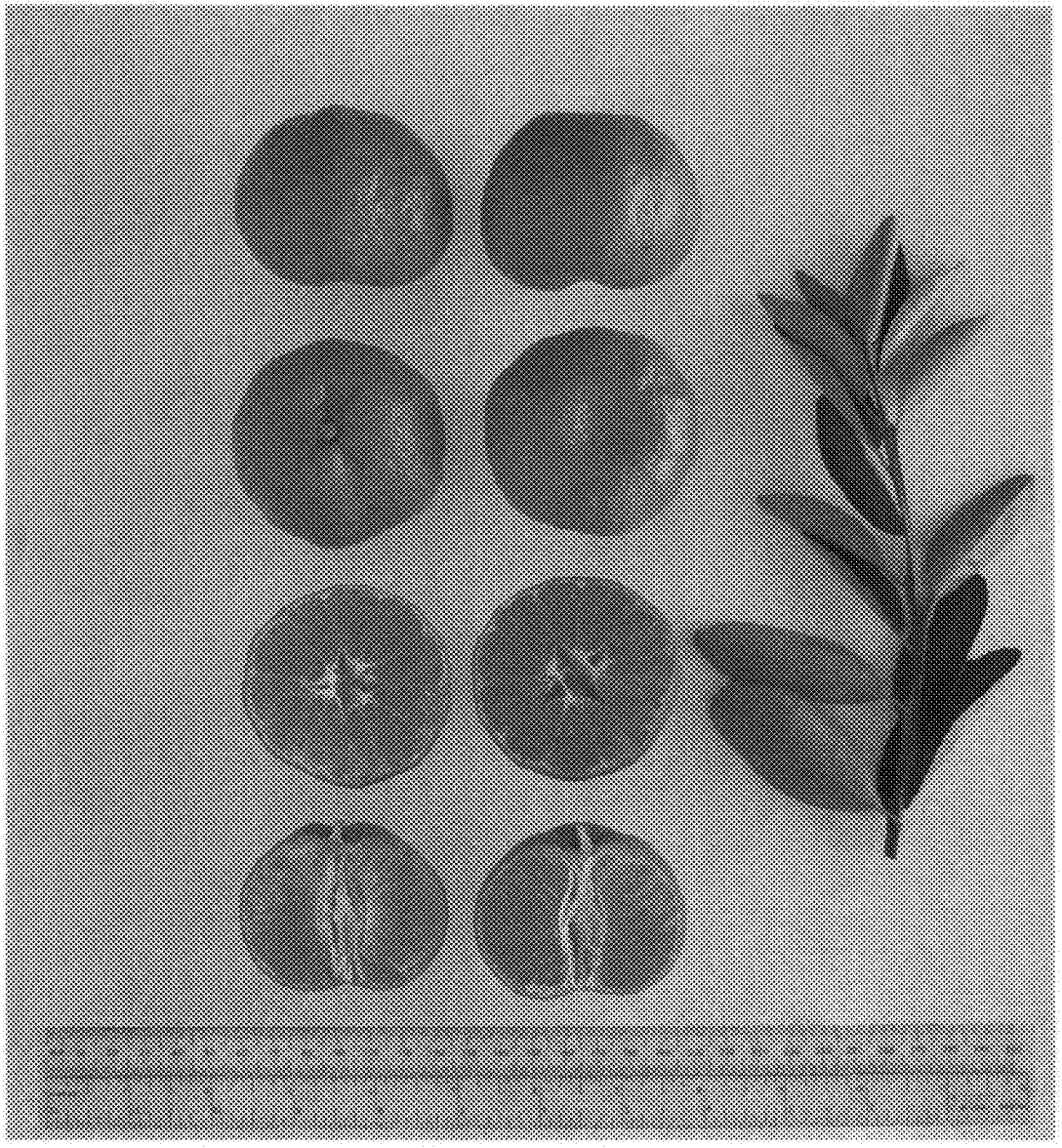
FIG. 1—Shows a typical specimen of the fruit, leaf, and stem of 'UFGlow' demonstrating the attractive shape and exterior coloration of the fruit above a ruler in a stem end view, a blossom end view, a fruit cut longitudinally to better demonstrate fruit shape, and a fruit cut at the equator to show peel thickness, flesh color, and carpels.
Figure 2:
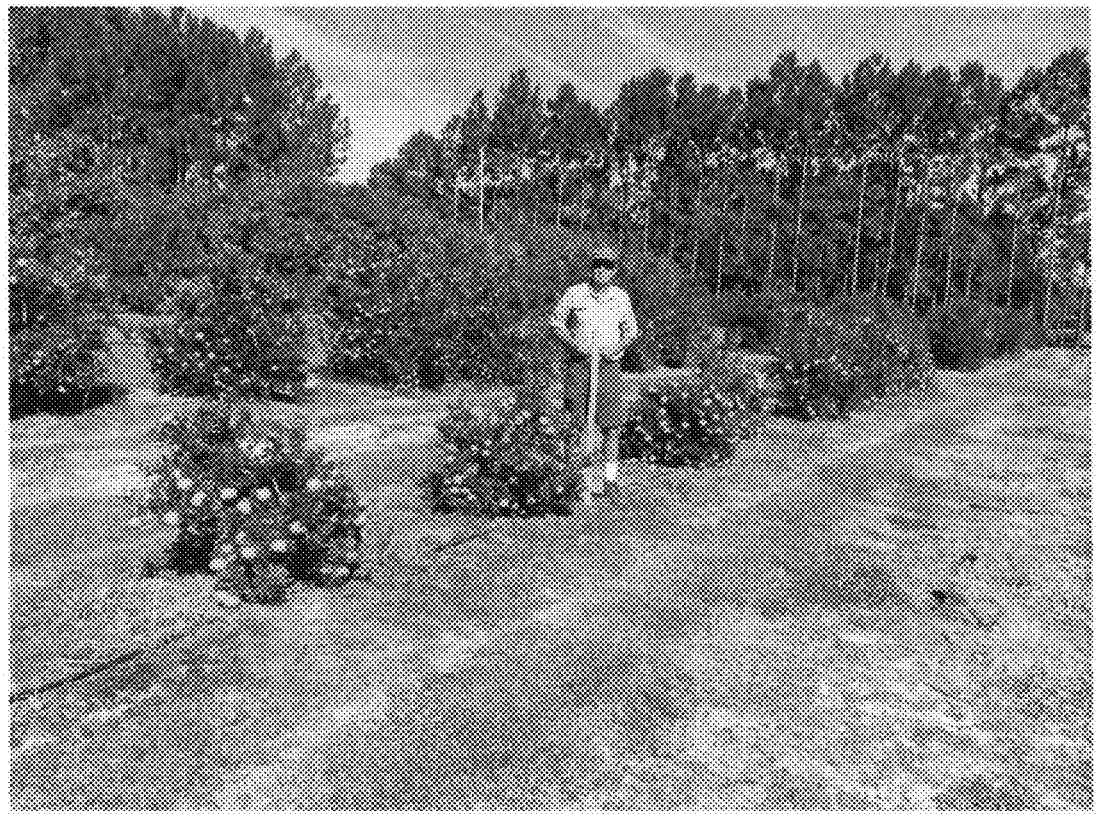
FIG. 2—Shows the overall plant growth habit.

The present botanical description is that of the variety grown for 4 years on 'Carrizo' rootstock under the ecological conditions prevailing in Gainesville, Fla.

PHENOTYPIC DESCRIPTION OF 'UFGLOW'

Tree:

*Ploidy*.—Diploid.

*Size*.—Trees have a medium-small stature.

*Vigor*.—Moderately vigorous; trees respond typically to irrigation and fertilization. Tree growth of 1 to 2 feet in height and width occurs the first few growing seasons depending on rootstock. Canopy is dense because branches are compact, resulting in a small tree.

*Density*.—Light to medium in branching habit. Weight of fruit will bend branches down considerably and may require pruning of lower branches, especially the first 3 to 4 crops.

*Form*.—Short, elliptic to oblong when not pruned.

*Hardiness*.—Evergreen and hardy with respect to typical winters in north central Florida.

*Bearer*.—Very productive annually without alternate bearing observed. Trees are self-fertile.

Trunk:

*Size*.—Medium-small trunk diameter, attaining a 12-cm diameter at a height of 50 cm at the end of 16 years growth on the original seedling tree, and 7 cm at a height of 50 cm at the end of 3 years growth on 'Carrizo' rootstock in Gainesville, Fla.

*Bark color*.—Older bark gray, Dove (Pantone 15-0000).

Branches:

*Size*.—Strong growth of scaffold branches. Fruiting branches are mostly small diameter (2 to 4 mm) and twiggy.

*Color*.—New wood in spring flush is light green, Grasshopper Green (Pantone 18-0332). The previous summer wood is darker green, Chive (Pantone 19-0323).

*Thorns*.—Small thorns (1 to 2 mm in length) occur in the axils of some leaves from just below and slightly to one side of the axillary bud.

*Leaves*.—Small, 4.0 to 7.0 cm length, including the petiole; 2.0 to 3.0 cm width. Measurements were made on shoots bearing fruit.

*Thickness*.—Average for many *citrus* varieties. Not noticeably unusual.

*Form*.—Elliptic.

*Apex*.—Acute.

*Margin*.—Crenate, but more strongly in the distal half of the leaf blade.

*Base*.—Obtuse.

*Surface*.—Upper, glabrous; Lower, less glabrous, with medium veins that are pinnately netted.

*Color*.—Lower surface is light green, Spinach Green (Pantone 16-0439); Upper surface is slightly darker green, Artichoke Green (Pantone 18-0125).

*Petiole*.—Average 8 mm length and 1 mm in diameter with small wings of 0.5 mm on each side with similar colors to the corresponding leaf surface.

*Leaflets*.—Single.

*Arrangement*.—Alternate.

*Leaf retention*.—Evergreen.

Flowers:

*Blossom period*.—Flowers in mid to late March most years in Gainesville, but occurring over a 10 to 15 day period. Time and length of bloom are dependent on ambient temperature.

*Type*.—Hermaphrodite (perfect flower).

*Aroma*.—Highly fragrant.

*Density*.—Abundant bouquet bloom in axil of leaves, but also abundant leafy bloom on new growth.

*Size*.—Average flower diameter, 2.7 cm; average petal length, 14 mm; width, 6 mm.

*Texture*.—Waxy and smooth; margins are smooth.

*Color*.—White, Antique white (Pantone 11-0105) at flower opening.

*Flower parts*.—Pistil size, shape and color are within the range of standard commercial varieties. There are 5 sepals and petals. Sepals average 2 mm in length and 3 mm wide at the base, and acute at the distal end. Sepals are pale green, Frozen Dew (Pantone 13-0513) with a glaucus margin. Sepals and petals are glabrous. Pistils are 1 per flower. Pistil length (from tip of stigma to base of ovary) averages 8 mm. Ovary is green, Bright Chartreuse (Pantone 14-0445), pedicel is light green, Apple Green (Pantone 15-0543), and stigmatic head is yellow, Lemon Drop (Pantone 12-0736). Flower pedicel is 4 to 5 mm in length.

*Stamen*.—Anthers are yellow, Snapdragon (Pantone 13-0840) at flower opening. Number of anthers averages 20. Filaments are white, similar to petals, and length is 7 to 8 mm.

*Pollen*.—Abundant and bright yellow, Banana (Pantone 13-0947).

*Fertility*.—Fully self fertile, no cross pollination is required. Fruit set is abundant.

Fruit:

*Location*.—Most fruit are borne on shoot terminals.

*Maturity when described*.—Nov. 1, 2014 in Gainesville, Fla.

*Date of picking*.—First, mid-October, 2014; Last, Nov. 15, 2014 in Gainesville. Fruit peel becomes puffy and flesh softens indicating over ripeness by December 1.

*Size*.—Uniform, small, averaging 120 g per fruit. Size varies with fruit number per tree, soil type, climatic conditions, and cultural practices. Form is slightly squat with a low tendency to sheep nose in some seasons. Average equatorial diameter: 5.5 to 7.5 cm. Average polar length (stem to distal end): 4.5 to 6.0 cm.

*Peel*.—Thickness: Epidermis and albedo are medium-thick (3 to 4 mm on average). Tenacity: Loose flesh, peels readily. Color: Orange, Flame Orange (Pantone 15-1157) on fully colored fruit usually by November, but changing from mostly green skin in mid November, depending on incidence of low temperatures. Tendency to crack: None observed. Epidermis: Glabrous with small oil glands slightly lighter than skin between glands, with approximately 75 oil glands per square cm. Epidermis is susceptible to sunburn on exposed fruit surfaces, particularly on upper southwest sides of young trees.

*Flesh*.—Ripens: Evenly within each fruit. Texture: Firm and extremely juicy when fully ripe. Juice vesicles: 1 cm in length on average, and tender. Eating quality: Good, sweet, and slightly acidic, with little bitterness. Soluble solids average from 8 to 9 brix at peak ripening in mid October. Color: Orange, Apricot (Pantone 15-1153). Juice is similar in color. Carpels (segments): Number varies from 9 to 12, averaging 10 per fruit. Calyx: Persistent at stem end of fruit, with some pilose pubescence remaining upon ripening, and 6 to 7 mm in diameter with green, Sweet Pea Green (Pantone 15-0531) at first harvest, but yellowing and browning at tip as fruit ripen. Seed: Fruit are typically seedless. On occasion, small aborted seeds are observed. Seed coat color is light brown, Mustard Gold (Pantone 16-1133) when first removed from the fruit. Cotyledon color is green, Olive Green (Pantone 17-0535). Seed size is 2 mm in length, 1 mm in width, and 1 mm thick.

Use: Commercial production, ripening in Gainesville, Fla. area by mid October and potentially mid September in the Ft. Pierce, Fla. area.

Resistance to disease: High leaf and fruit resistance to scab incited by *Elsinoe fawcettii*, Alternaria brown spot incited by *Alternaria alternata*, and melanose incited by *Diaporthe citri*.

What is claimed is:

1. A new and distinct mandarin tree called 'UFGlow' as illustrated and described herein.

* * * * *